(12) United States Patent
Kerns et al.

(10) Patent No.: US 11,717,705 B1
(45) Date of Patent: Aug. 8, 2023

(54) PHANTOM HOLDER FOR RADIATION THERAPY SYSTEM

(71) Applicant: VARIAN MEDICAL SYSTEMS, INC., Palo Alto, CA (US)

(72) Inventors: James Kerns, Katy, TX (US); Niklaus Schneider, Bonstetten (CH); Todd G Holmes, Bethlehem, PA (US); Christian Stamm, Baden (CH)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

(21) Appl. No.: 17/878,645

(22) Filed: Aug. 1, 2022

Related U.S. Application Data

(63) Continuation of application No. 17/721,331, filed on Apr. 14, 2022.

(51) Int. Cl.
*A61N 5/10* (2006.01)

(52) U.S. Cl.
CPC .... *A61N 5/1075* (2013.01); *A61N 2005/1076* (2013.01)

(58) Field of Classification Search
CPC ............. A61N 5/1075; A61N 2005/1076
See application file for complete search history.

(56) References Cited

U.S. PATENT DOCUMENTS

| | | | | |
|---|---|---|---|---|
| 5,107,839 A | * | 4/1992 | Houdek | A61N 5/1049 600/417 |
| 6,799,068 B1 | * | 9/2004 | Hartmann | A61N 5/1071 607/2 |
| 7,786,433 B2 | | 8/2010 | Gunzert-Marx et al. | |
| 9,643,029 B2 | | 5/2017 | Scheib | |
| 10,898,158 B2 | | 1/2021 | Constantin et al. | |
| 2003/0185348 A1 | * | 10/2003 | Ghelmansarai | A61N 5/1049 378/65 |
| 2005/0013406 A1 | * | 1/2005 | Dyk | A61N 5/1049 378/65 |
| 2005/0077459 A1 | * | 4/2005 | Engler | A61N 5/1048 250/252.1 |
| 2005/0080332 A1 | * | 4/2005 | Shiu | A61B 6/032 600/417 |
| 2005/0211889 A1 | * | 9/2005 | Varchena | G01R 33/58 250/252.1 |
| 2006/0285639 A1 | * | 12/2006 | Olivera | A61N 5/1042 378/65 |

(Continued)

OTHER PUBLICATIONS

"Introducing RadMachine Webinar", Apr. 8, 2022, Retrieved from the <URL: https://resources.radformation.com/webinars?hsLang=en.>.

(Continued)

*Primary Examiner* — Blake C Riddick
(74) *Attorney, Agent, or Firm* — Su IP Consulting

(57) ABSTRACT

An apparatus in a radiation therapy system includes: a base configured to support a first quality assurance phantom at a first position and a second quality assurance phantom at a second position; and at least one coupling element. The at least one coupling element is configured to: mate with at least one indexing feature of a first patient treatment couch of the radiation therapy system; and fix a position of the base relative to the first patient treatment couch.

19 Claims, 12 Drawing Sheets

(56) References Cited

U.S. PATENT DOCUMENTS

| | | | | |
|---|---|---|---|---|
| 2008/0219410 A1 | * | 9/2008 | Gunzert-Marx | A61N 5/1048 378/207 |
| 2008/0240364 A1 | * | 10/2008 | Main | A61N 5/1048 250/252.1 |
| 2009/0168960 A1 | * | 7/2009 | Jongen | A61N 5/1049 378/65 |
| 2011/0085645 A1 | * | 4/2011 | Paidi | A61B 6/584 378/207 |
| 2012/0312961 A1 | * | 12/2012 | Raleigh | A61B 6/542 250/206 |
| 2012/0316379 A1 | * | 12/2012 | Raleigh | A61N 5/1049 600/1 |
| 2012/0316423 A1 | * | 12/2012 | Raleigh | A61B 5/0077 600/407 |
| 2013/0006036 A1 | * | 1/2013 | Raleigh | A61N 5/1077 382/128 |
| 2013/0068939 A1 | * | 3/2013 | Schule | A61N 5/1075 250/252.1 |
| 2013/0235969 A1 | * | 9/2013 | Winter | A61N 5/1079 378/4 |
| 2014/0016759 A1 | * | 1/2014 | Ngar | A61B 6/584 378/207 |
| 2015/0071408 A1 | * | 3/2015 | Ebstein | A61N 5/1075 378/65 |
| 2015/0085993 A1 | * | 3/2015 | Scheib | A61N 5/1071 378/207 |
| 2015/0343240 A1 | * | 12/2015 | Beaumont | A61N 5/1075 378/207 |
| 2015/0343241 A1 | * | 12/2015 | Han | G06T 5/003 378/205 |
| 2015/0360056 A1 | * | 12/2015 | Xing | A61N 5/1049 250/362 |
| 2016/0023019 A1 | * | 1/2016 | Filiberti | A61N 5/107 600/1 |
| 2016/0059042 A1 | * | 3/2016 | Russo | A61N 5/1031 600/1 |
| 2016/0129283 A1 | * | 5/2016 | Meir | G06T 7/0012 348/46 |
| 2017/0080254 A1 | * | 3/2017 | Scheib | A61N 5/1049 |
| 2017/0312547 A1 | * | 11/2017 | Wong | A61N 5/1082 |
| 2018/0140272 A1 | * | 5/2018 | Ruchala | A61B 6/4435 |
| 2018/0200537 A1 | * | 7/2018 | Gustafsson | A61N 5/1071 |
| 2019/0054322 A1 | * | 2/2019 | Yang | A61N 5/1081 |
| 2019/0076673 A1 | * | 3/2019 | Lu | A61N 5/1077 |
| 2019/0329072 A1 | * | 10/2019 | Magro | G01T 1/161 |
| 2020/0061392 A1 | * | 2/2020 | Filiberti | A61N 5/1045 |
| 2020/0179723 A1 | * | 6/2020 | Gagneur | A61N 5/1075 |
| 2020/0315567 A1 | * | 10/2020 | Constantin | A61B 6/589 |
| 2020/0346042 A1 | * | 11/2020 | Maltz | G06T 11/005 |
| 2020/0353290 A1 | * | 11/2020 | Çelik | A61N 5/1075 |
| 2021/0101026 A1 | * | 4/2021 | Çelik | A61B 6/583 |
| 2021/0228910 A1 | * | 7/2021 | Subrahmanyam | A61N 5/1081 |
| 2021/0236855 A1 | * | 8/2021 | Adamson | A61N 5/1045 |
| 2022/0096869 A1 | * | 3/2022 | Molloy | H05H 7/02 |
| 2022/0203131 A1 | * | 6/2022 | Wang | A61N 5/1075 |
| 2022/0219018 A1 | * | 7/2022 | Yan | A61N 5/1075 |

OTHER PUBLICATIONS

Christian Stamm et al., Non-Published U.S. Appl. No. 17/560,005, filed Dec. 22, 2021, 52 pages, Varian Medical Systems International AG.

\* cited by examiner

PHANTOM HOLDER FOR RADIATION THERAPY SYSTEM

CROSS-REFERENCE TO RELATED APPLICATION

The present application is a continuation under 35 U.S.C. § 120 of U.S. patent application Ser. No. 17/721,331, filed Apr. 14, 2022. The aforementioned U.S. patent application is incorporated herein by reference.

BACKGROUND

Unless otherwise indicated herein, the approaches described in this section are not prior art to the claims in this application and are not admitted to be prior art by inclusion in this section.

Radiation therapy (also called radiotherapy) is a cancer treatment that employs high doses of ionizing radiation, such as X-rays or high-energy electrons, protons, or other heavy charged particles, to kill cancer cells. In general, radiation therapy is a localized treatment for a specific anatomical target, such as a cancerous tumor, and is ideally performed on a planning target volume (PTV) that spares the surrounding normal tissue from receiving doses above specified tolerances. In this way, the risk of damage to healthy tissue is minimized. Prior to the delivery of radiation therapy, an imaging system is typically employed to provide a three-dimensional image of the anatomical target and surrounding area. From such imaging, the size and mass of the anatomical target can be estimated, the PTV determined, and an appropriate treatment plan generated using a treatment planning system.

So that a planned radiation dose is supplied accurately to the PTV during radiation therapy, a patient must be correctly positioned relative to the linear accelerator that provides the therapeutic radiation beam. For example, in many cases, for a successful radiation therapy treatment, the patient must be precisely positioned so that the PTV is located at the isocenter about which the linear accelerator rotates. To that end, the location of the PTV is pinpointed via treatment planning images that are generated at the time of treatment. Consequently, imaging accuracy is an important factor for accurately implementing a planned radiation dose.

In addition, to accurately supply a planned radiation dose, the spatial distribution of delivered radiation dose within the patient must closely match the spatial distribution of the planned radiation dose. Therefore, the actual performance of the radiation source or sources that generate the planned radiation dose must closely match the radiation source performance that is assumed when generating a treatment plan.

In light of the above, various phantoms are commonly employed for the characterization and calibration of radiation delivery devices, including radiation sources for imaging and treatment beams. For example, certain phantoms may be used to measure geometric characteristics of a radiation therapy system, such as radiation-light field phantoms; certain phantoms may be used to measure dosimetry characteristics of a radiation therapy system; and certain phantoms may be used to measure imaging characteristics of a radiation therapy system, such as planar image quality phantoms and/or computed tomography (CT) image quality phantoms. Further, dosimetry phantoms may be used in the verification of planned or otherwise modeled dose distributions. Consequently, phantoms are important in ensuring safe and effective radiation therapy for the patient.

SUMMARY

According to various embodiments, a phantom holder is configured to support multiple quality assurance (QA) phantoms in known, pre-defined locations and orientations relative to a radiation therapy system. The phantom holder includes one or more coupling elements that securely attach the phantom holder to a treatment couch of the radiation therapy system in a known, reproducible location. Therefore, the multiple QA phantoms supported by the phantom holder can each be remotely positioned for specific QA measurement(s) associated with that phantom. As a result, the phantom holder enables execution of a sequence of multiple automated measurements by positioning a first QA phantom via the treatment couch and acquiring one or more measurements, positioning a second QA phantom via the treatment couch and acquiring one or more measurements, and so on. Such a sequence of measurements can be automated, so that the clinician is no longer required to reenter the treatment room to position each QA phantom.

According to some embodiments, an apparatus in a radiation therapy system includes: a base configured to support a first quality assurance phantom at a first position and a second quality assurance phantom at a second position; and at least one coupling element. The at least one coupling element is configured to: mate with at least one indexing feature of a first patient treatment couch of the radiation therapy system; and fix a position of the base relative to the first patient treatment couch.

According to some embodiments, a computer-implemented method for performing a sequence of multiple QA processes on a radiation therapy system includes: selecting a first QA process from the sequence of multiple QA processes; in response to selecting the first QA process, moving a treatment couch of the radiation therapy system to a first couch position associated with the first QA process, so that a first phantom associated with the first QA process is disposed at a first test location; performing the first QA process while the first phantom is disposed at the first test location; upon completion of the first QA process, selecting a second QA process from the sequence of multiple QA processes; in response to selecting the second QA process, moving a treatment couch of the radiation therapy system to a second couch position associated with the second QA process, so that a second phantom associated with the second QA process is disposed at a second test location; and performing the second QA process while the second phantom is disposed at the second test location.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
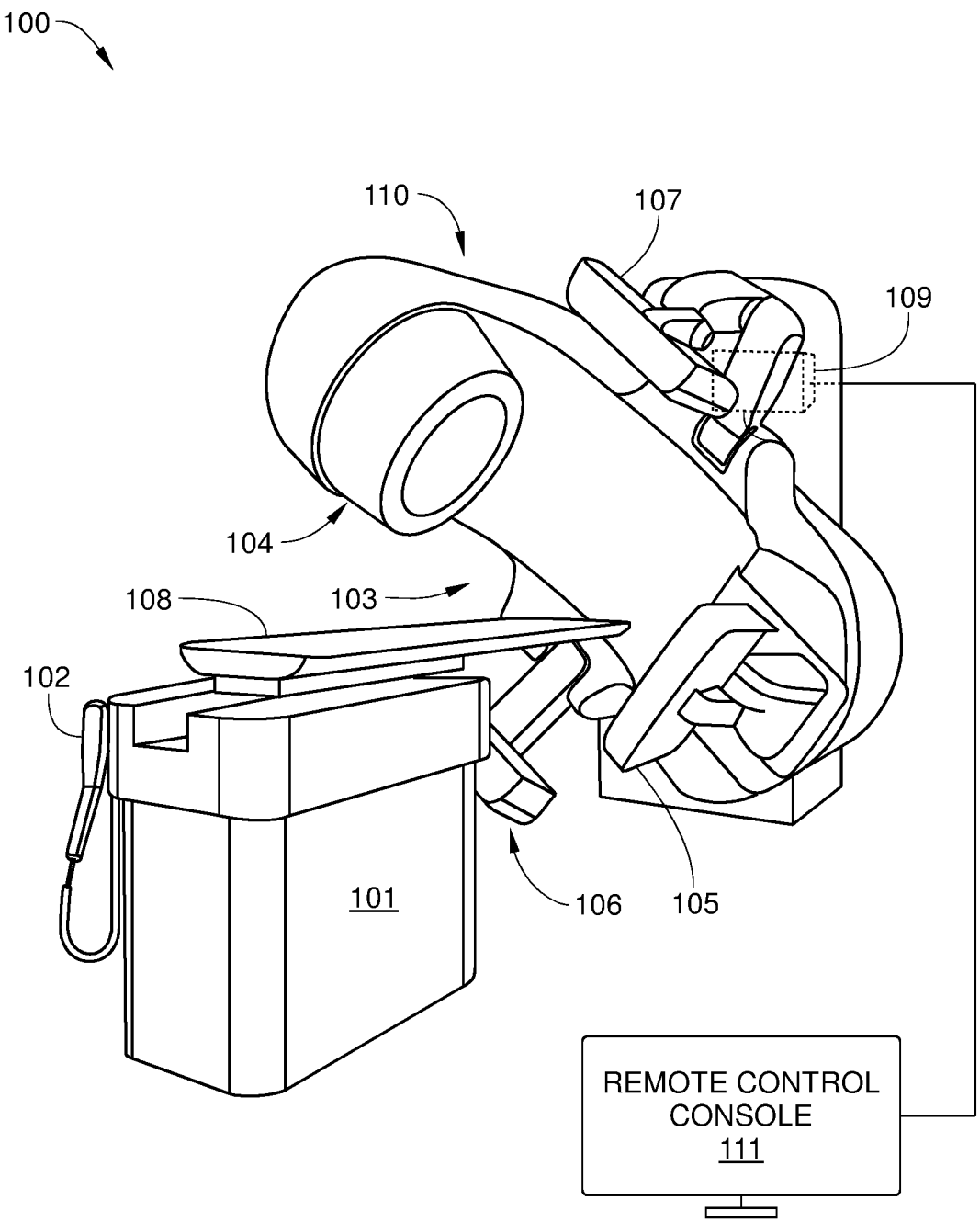
FIG. 1 is a perspective view of a radiation therapy system that can beneficially implement various embodiments.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

INTRODUCTION

As noted previously, various phantoms are commonly employed for the characterization and calibration of radiation delivery devices, in the verification of planned dose distributions, and for other quality assurance (QA) checks of a radiation therapy system. For example, imaging phantoms can quantify how well a particular imaging system can differentiate soft tissue from bones and how accurately slices of a patient anatomy can be resolved. Other imaging phantoms can be employed that simulate patient breathing, enable measurement of planar image quality, and indicate whether the light field of a radiation therapy system is properly aligned with the radiation field of the radiation therapy system.

In conventional QA practice, for a particular radiation source or imaging test, each phantom is carefully positioned on a couch or patient support of a radiation therapy system and manually moved to a specified test location in a beam path via the couch, and precisely oriented relative to the radiation therapy system (for example using the system's patient alignment lasers). The clinician then leaves the treatment room and selects and initiates an appropriate imaging or treatment dose protocol for the particular test. Typically, a suite of multiple QA tests are performed on a radiation therapy system together, for example during a periodic performance check. Thus, for each phantom that is required to complete the suite of tests, the clinician must make a separate trip into the treatment room and position the next phantom, a process that can be time-consuming and prone to error. For example, for a particular test, an incorrect phantom may be selected, the phantom may be inaccurately positioned on the couch (and therefore may not be moved to the correct test location), and/or the wrong QA test may be selected. If any of the above issues occurs, the clinician must reenter the treatment room and repeat the set-up procedure for that particular test.

Accordingly, there is a need in the art for improved techniques positioning phantoms for testing a radiation therapy system.

System Overview

FIG. 1 is a perspective view of a radiation therapy system 100 that can beneficially implement various embodiments. Radiation therapy (RT) system 100 is a radiation system that may be configured to detect intra-fraction motion in near-real time using either optical or X-ray imaging techniques, or both. Thus, in some embodiments, RT system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) 104 that generates an MV treatment beam of high energy X-rays or other radiation, one or more kilovolt (kV) X-ray sources 106, one or more imaging panels 107 (e.g., an X-ray imager), and an MV electronic portal imaging device (EPID) 105. By way of example, RT system 100 is described herein configured with a C-arm gantry 110 capable of infinite rotation via a slip ring connection. In other embodiments, RT system 100 can be configured with a circular gantry mounted on a drive stand, or any other technically feasible configuration that enables radiation therapy and imaging of a PTV.

In some embodiments, RT system 100 is capable of X-ray imaging of a target volume immediately prior to and/or during application of an MV treatment beam, so that an image-guided radiation therapy (IGRT) and/or an intensity-modulated radiation therapy (IMRT) process can be performed using X-ray imaging. For example, in some embodiments, such processes can include kV imaging of a PTV in conjunction with imaging generated by the MV treatment beam. RT system 100 may include one or more touchscreens (not shown) for patient information verification, couch motion controls 102, a radiation area 103, a couch positioning assembly 101, a couch 108 disposed on couch positioning assembly 101, and an image acquisition and treatment control computer 109, all of which are disposed within a treatment room. RT system 100 further includes a remote control console 111, which is disposed outside the treatment room and enables treatment delivery and patient monitoring from a remote location. Couch positioning assembly 101 is configured to precisely position couch 108 with respect to radiation area 103. Motion controls 102 include input devices, such as buttons and/or switches, that enable a user to operate couch positioning assembly 101 to automatically and precisely position couch 108 to a predetermined location with respect to radiation area 103. Motion controls 102 also enable a user to manually position couch 108 to a particular location, such as a planned treatment position for a patient or anatomical target.

Figure 2:
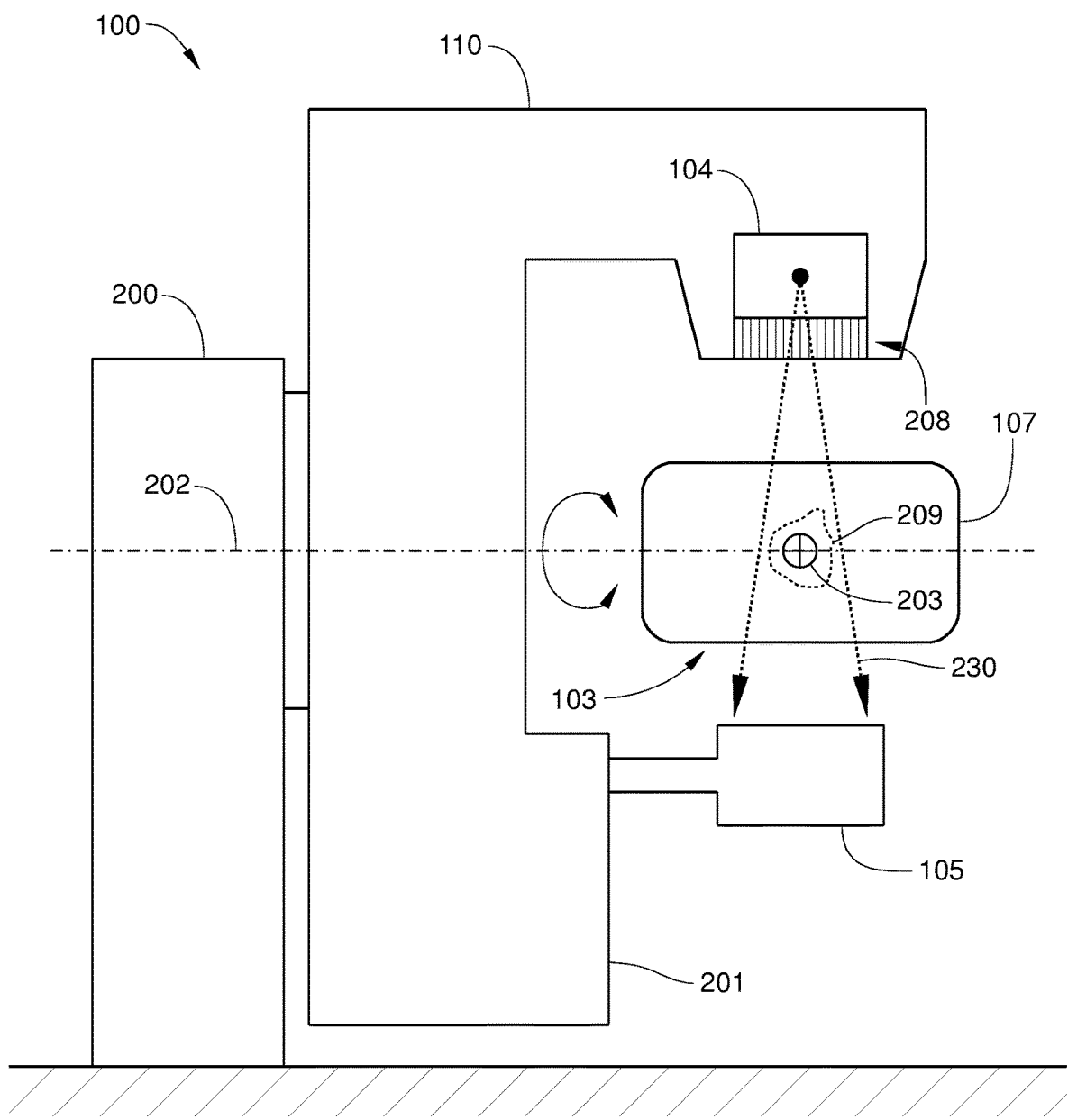
FIG. 2 schematically illustrates a side view of the radiation therapy system of FIG. 1, according to various embodiments.

FIG. 2 schematically illustrates a side view of RT system 100, according to various embodiments. As shown, RT system 100 includes a base stand 200 and C-arm gantry 110. In FIG. 2, couch positioning assembly 101, couch 108, and X-ray source 106 are omitted for clarity. Base stand 200 is a fixed support structure for components of RT treatment system 100, including C-arm gantry 110 and a drive system (not shown) for rotatably moving C-arm gantry 110 about a horizontal rotation axis 202. Base stand 200 rests on and/or is fixed to a support surface that is external to RT treatment system 100, such as a floor of an RT treatment facility. C-arm gantry 110 is rotationally coupled to base stand 200 and is a support structure on which various components of RT system 100 are mounted, including LINAC 104, EPID 105, imaging X-ray source 106 (not shown in FIG. 2), and imaging panel 107. During operation of RT treatment system 100, C-arm gantry 110 rotates about radiation area 103 when actuated by the drive system.

Imaging X-ray source 106 is configured to direct a conical beam of X-rays, referred to herein as imaging X-rays (not shown in FIG. 2 for clarity), through an isocenter 203 of RT system 100 to imaging panel 107. Ideally, isocenter 203 corresponds to the location of a target volume 209 to be treated, such as a PTV, a gross tumor volume (GTV), a clinical target volume (CTV), and/or an internal target volume (ITV), among others. The GTV depicts the position and extent of the gross tumor, for example portions of the tumor that can be seen or imaged; the CTV includes the GTV and an additional margin for sub-clinical disease spread, which is generally not imageable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by X-ray imaging of a specified region of patient anatomy as described below.

In the embodiment illustrated in FIG. 2, imaging panel 107 is depicted as a planar device, whereas in other embodiments, imaging panel 107 can have a curved configuration. In the embodiment illustrated in FIGS. 1 and 2, RT system 100 includes a single imaging panel and a single corresponding imaging radiation source in addition to EPID 105. In other embodiments, RT system 100 can include two or more imaging panels, each with a corresponding imaging radiation source. Further, in some embodiments, couch positioning assembly 101 is configured to rotate, pitch, roll, and/or translate couch 108 sequentially relative to isocenter 203 to one or more treatment positions. One such embodiment is described below in conjunction with FIG. 3.

Figure 3:
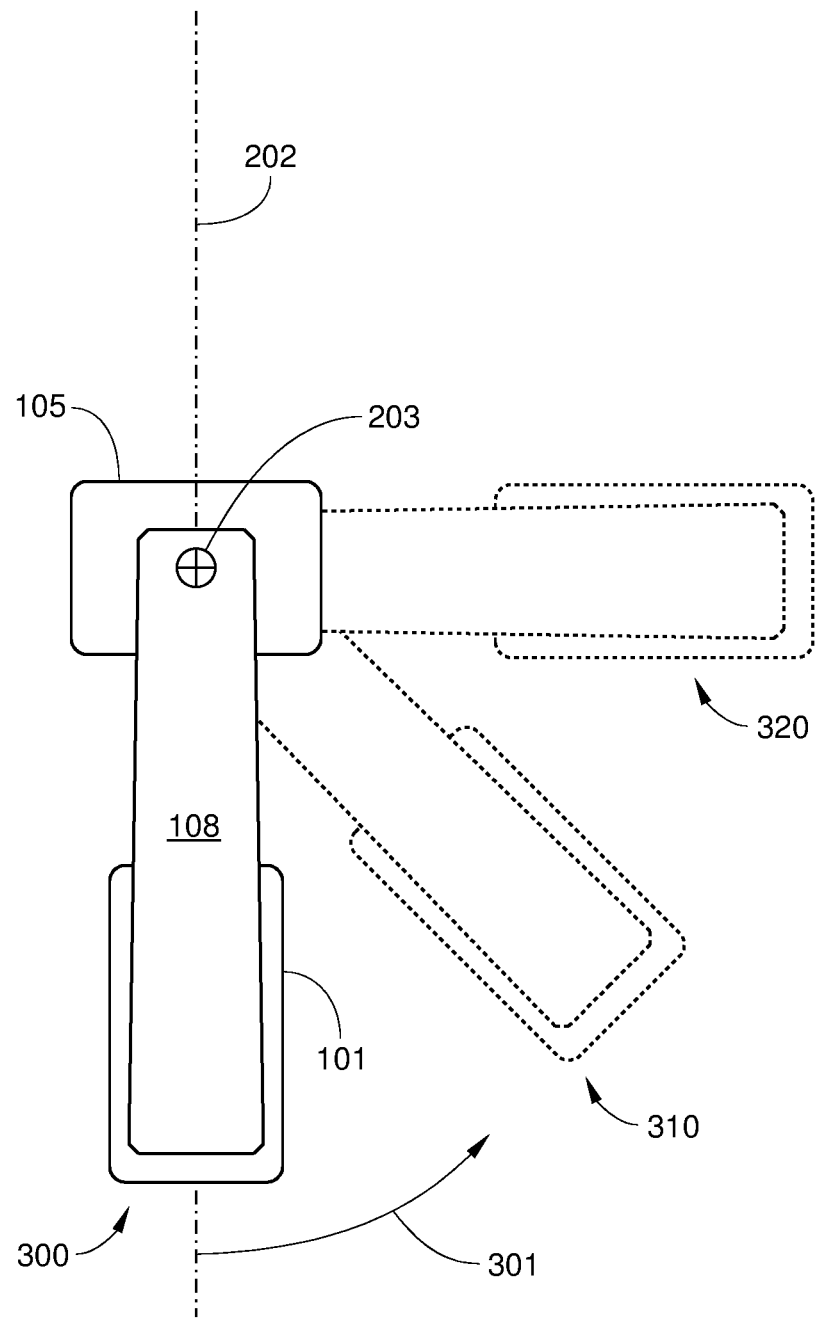
FIG. 3 schematically illustrates plan views of a couch of the radiation therapy system of FIG. 1 in various treatment positions, according to various embodiments.

FIG. 3 schematically illustrates plan views of couch 108 in various treatment positions, according to various embodiments. FIG. 3 includes a plan view of couch 108 in a neutral position 300, in which couch 108 is in line with horizontal rotation axis 202 of C-arm gantry 110, a first rotated position 310 (dashed lines), in which couch 108 is rotated 45 degrees from neutral position 300, and a second rotated position 320 (dashed lines), in which couch 108 is rotated 90 degrees from neutral position 300. For reference, EPID 105 and isocenter 203 are both included in FIG. 3. As shown, couch positioning assembly 101 rotates couch 108 about isocenter 203 to a couch rotational angle 301 from neutral position 300. Couch rotational angle 301 can be, for example, up to about 90 degrees.

Returning to FIG. 2, LINAC 104 typically includes one or more of an electron gun for generating electrons, an accelerating waveguide, an electron beam target, an electron beam transport means (such as a bending magnet) for directing the electron beam to the electron beam target, and/or a collimator assembly 208 for collimating and shaping a treatment beam 230 that originates from the electron beam target. Collimator assembly 208 typically includes one or more of a primary collimator that defines the largest available circular radiation field for treatment beam 230, a secondary collimator for providing a rectangular or square radiation field at isocenter 203 (for example via X-jaws and Y-jaws), and a multileaf collimator (MLC) for conforming treatment beam 230 to a PTV or other anatomical target.

During radiation treatment, LINAC 104 is configured to generate treatment beam 230, which can include high-energy radiation (for example MV X-rays or MV electrons). In other embodiments, treatment beam 230 includes electrons, protons, and/or other heavy charged particles, ultra-high dose rate X-rays (e.g., for FLASH radiotherapy), and/or microbeams for microbeam radiation therapy. In addition, imaging panel 107 is configured to receive imaging radiation and generate suitable projection images therefrom. Further, in some embodiments, as treatment beam 230 is directed to isocenter 203 while C-arm gantry 110 rotates through a treatment arc, image acquisitions can be performed via EPID 105 to generate image data for target volume 209. For example, in such embodiments, EPID 105 generates one or more projection images of target volume 209 and/or a region of patient anatomy surrounding target volume 209. Thus, projection images (e.g., 2D X-ray images) of target volume 209 can be generated during portions of an IGRT or IMRT process via imaging panel 107 and/or EPID 105. Such projection images can then be employed to construct or update portions of imaging data for a digital volume that corresponds to a three-dimensional (3D) region that includes target volume 209. That is, a 3D image of such a 3D region is reconstructed from the projection images. In some embodiments, cone-beam computed tomography (CBCT) and/or digital tomosynthesis (DTS) can be used to process the projection images generated by imaging panel 107.

Quality Assurance Phantom Holder

According to various embodiments, a phantom holder is configured to support multiple QA phantoms in known, pre-defined locations and orientations while securely attaching to a treatment couch, such as couch 108, in a known, reproducible location. Various embodiments are described below in conjunction with FIGS. 4-9.

Figure 4:
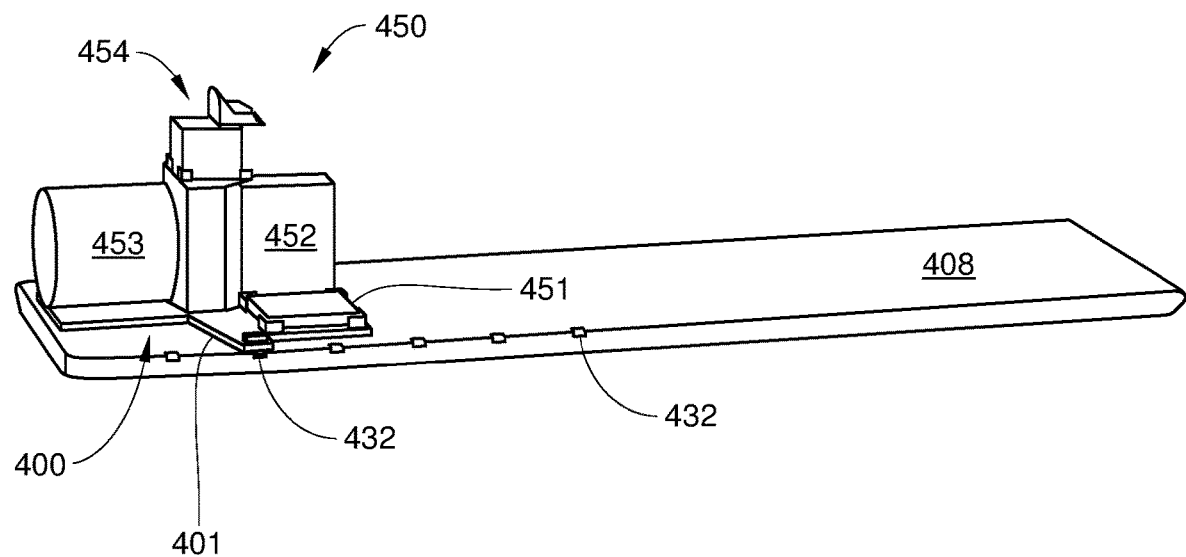
FIG. 4 is a perspective view of a phantom holder positioned on a treatment couch and loaded with multiple quality assurance phantoms, according to various embodiments.
Figure 5:
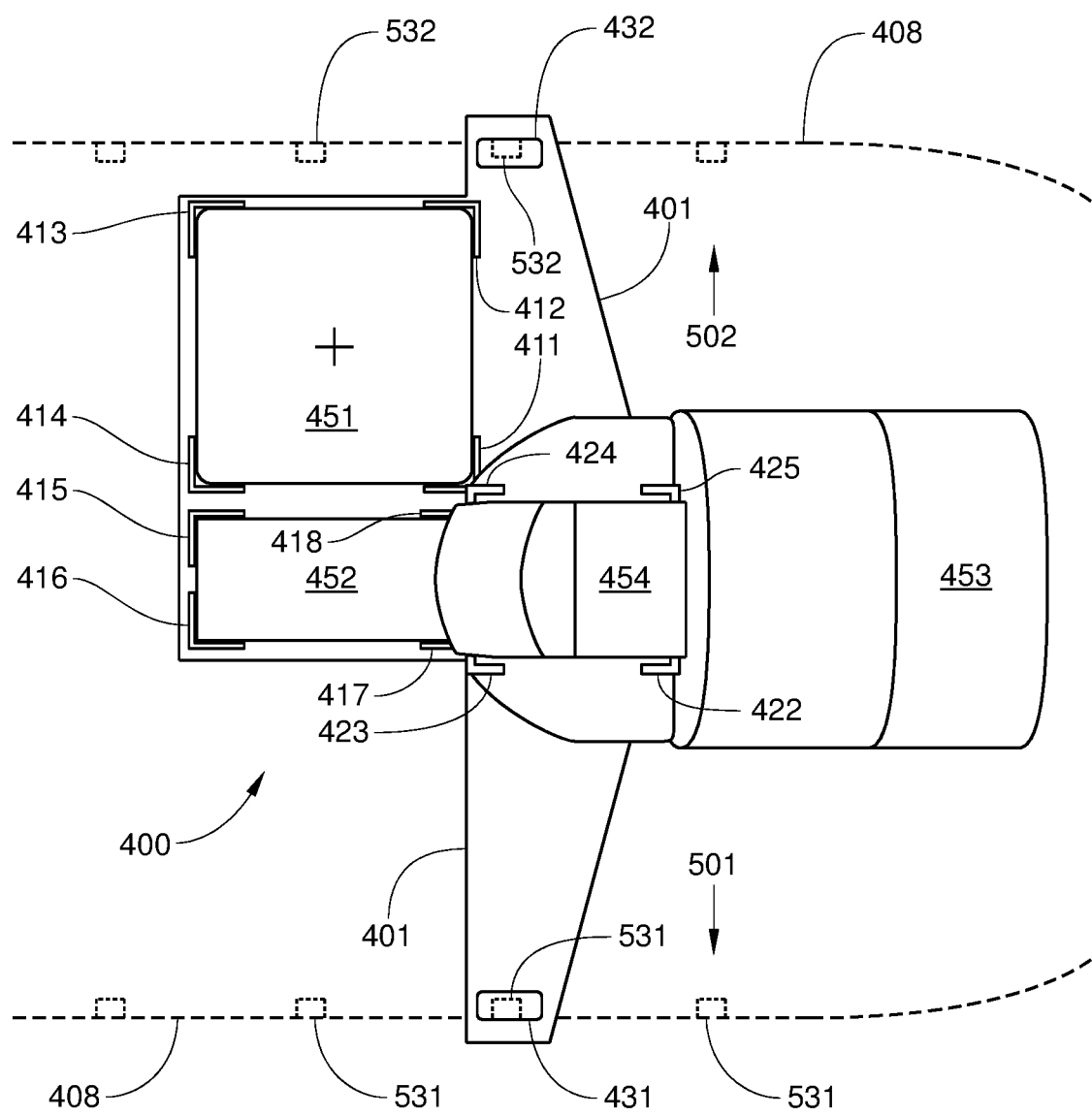
FIG. 5 is a plan view of the phantom holder of FIG. 4 positioned on a treatment couch and loaded with quality assurance phantoms, according to various embodiments.
Figure 6:
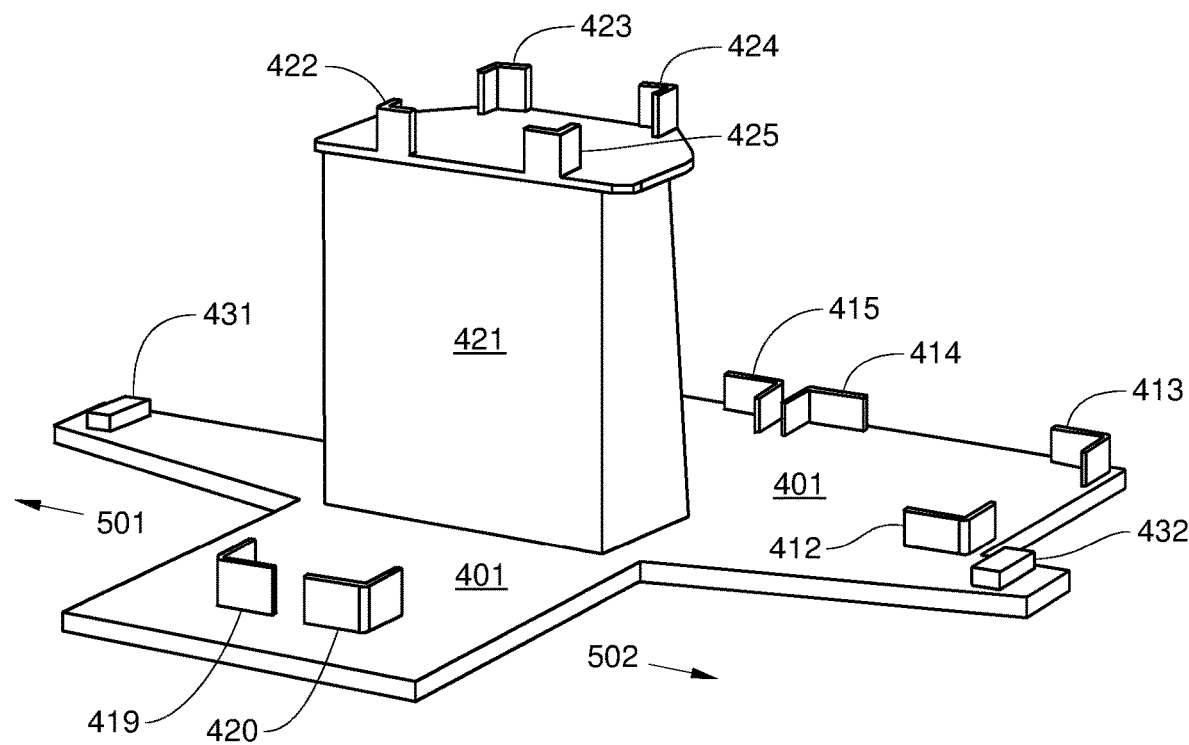
FIG. 6 is a perspective view of the phantom holder of FIG. 4 without quality assurance phantoms, according to various embodiments.

FIG. 4 is a perspective view of a phantom holder 400 positioned on a treatment couch 408 and loaded with multiple QA phantoms 451-454 (referred to collectively herein as QA phantoms 450), according to various embodiments; FIG. 5 is a plan view of phantom holder 400 positioned on treatment couch 408 and loaded with QA phantoms 450, according to various embodiments; and FIG. 6 is a perspective view of a phantom holder 400 without QA phantoms 450, according to various embodiments. Phantom holder 400 supports multiple QA phantoms 450 and includes a base 401, one or more positioning elements 411-425 (referred to collectively herein as positioning elements 410), and one or more coupling elements 431 and 432. In the embodiment illustrated in FIG. 4, phantom holder 400 is configured to support four QA phantoms 450, but in other embodiments, phantom holder 400 can be configured to support more than four QA phantoms 450 or less than four QA phantoms.

Each QA phantom 450 is a specific type of QA phantom that enables one or more tests or measurements associated with the imaging and/or dosimetric capabilities and/or the geometric positioning accuracy of a radiation therapy system, such as RT system 100. As such, QA phantoms 450 can include various heterogeneous phantom types, including QA phantoms that enable testing of CBCT imaging capabilities, QA phantoms that enable kV and MV image quality checks, QA phantoms that enable radiation/light-field checks, QA phantoms that enable respiration rate and gating checks, and/or the like. Thus, in some embodiments, a QA phantom 450 is configured for a measurement or test that includes a static position of an imaging system, such as QA phantom 451 or QA phantom 452. Alternatively or additionally, in some embodiments, a QA phantom 450 is configured for a measurement or test that includes a dynamic use of an imaging system via rotation of a gantry about the QA phantom, such as QA phantom 453. Alternatively or additionally, in some embodiments, a QA phantom 450 is configured for a measurement or test that includes optical sensors of a radiation therapy system, such as QA phantom 454. Alternatively or additionally, in some embodiments, a QA phantom 450 is configured for a measurement or test that includes directing ionizing radiation at the QA phantom, such as QA phantom 451, QA phantom 452, or QA phantom 453.

Base 401 is configured to support some or all of QA phantoms 450 while having little or no impact on measurements or tests performed on QA phantoms 450. Thus, in some embodiments, base 401 includes a material that is partially or completely radiologically transparent and is suitable for use in an environment in which exposure to ionizing radiation is frequent. For example, in such embodiments, the material does not cause significant X-ray scattering and does not degrade, discolor, and/or deform when exposed to ionizing radiation. In such embodiments, the material can be a polymer-based material that has sufficient rigidity to support QA phantoms 450 without deflecting significantly. Additionally or alternatively, in such embodiments, the material can be a material that facilitates one or more manufacturing processes. For example, in embodiments in which base 401 and/or other features of phantom holder 400 are printed via a three-dimensional printing process, the material of base 401 and/or the other features can be acrylonitrile butadiene styrene (ABS). In embodiments in which base 401 and/or other features of phantom holder 400 are formed via an injection molding process, the material of base 401 and/or the other features can be a thermoplastic that has sufficient rigidity and is suitable for frequent exposure to ionizing radiation.

Additionally or alternatively, in some embodiments, to further reduce impact on measurements or tests performed on QA phantoms 450, when a portion of base 401 and/or other components of phantom holder 400 are disposed within an active area of a particular QA phantom 450, the portion is configured so that effects on imaging by the portion are uniform over most or all images generated in association with that particular QA phantom 450. For example, in some embodiments, the portion is positioned, oriented, and/or otherwise configured so that an equal quantity of the material of that portion is irradiated for each irradiation-generated image generated in association with that particular QA phantom 450. Thus, in such embodiments, when multiple images are generated in association with that particular QA phantom 450, phantom holder 400 is configured so that the amount of irradiated material of base 401 and/or other components of phantom holder 400 is equal for all such images.

To further reduce impact on measurements or tests performed on QA phantoms 450, in some embodiments, base 401 is configured to be located outside any active areas of QA phantoms 450 when supporting some or all of QA phantoms 450. Examples of active areas for various QA phantoms is described below in conjunction with FIGS. 7-9.

Figure 7:
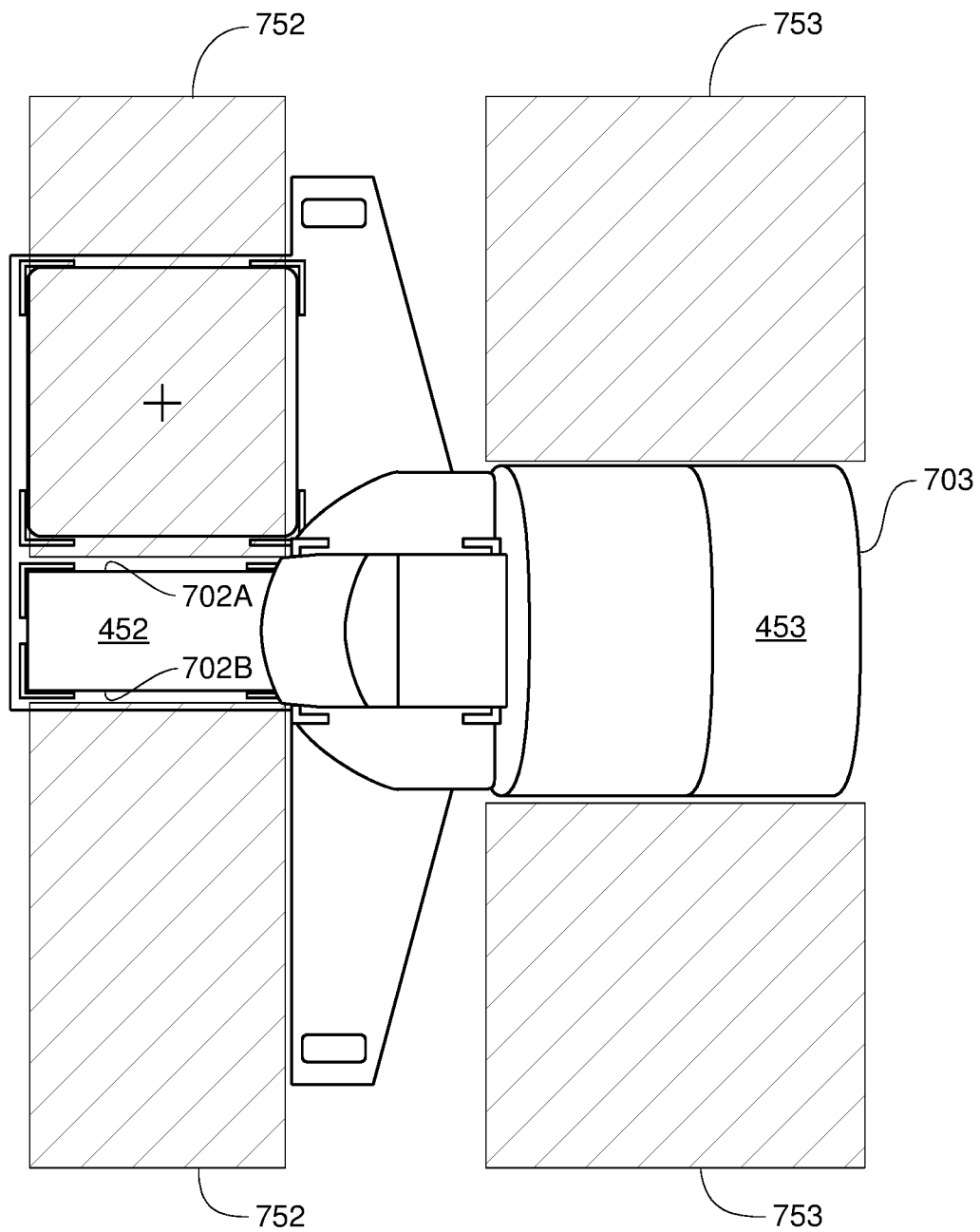
FIG. 7 is a plan view of a phantom holder and active areas associated with certain quality assurance phantoms, according to various embodiments.

FIG. 7 is a plan view of phantom holder 400 and active areas associated with certain QA phantoms 450, according to various embodiments. As shown, QA phantom 453 is a drum-shaped phantom, and has a cylindrical active area 753 (cross-hatched) or a partial cylindrical active area that extends around a curved surface 703 of QA phantom 453. In the embodiment illustrated in FIG. 7, cylindrical active area 753 indicates a region about QA phantom 453 through which, during certain measurements or tests, ionizing radiation is directed toward QA phantom 453. In such measurements or tests, a radiation source, such as X-ray source 106 or LINAC 104 of FIG. 2, is rotated about QA phantom 453 via a gantry, such as C-arm gantry 110 in FIG. 1. As noted, phantom holder 400 is configured so that components that include a material that can cause significant scattering of ionizing radiation are not disposed within cylindrical active area 753.

Also shown in FIG. 7 is QA phantom 452 and an associated active area 752 (cross-hatched) that extends away from a first vertical surface 702A and a second vertical surface 702B of QA phantom 452. In the embodiment illustrated in FIG. 7, active area 752 indicates regions adjacent to QA phantom 452 through which, during certain measurements or tests, ionizing radiation is directed toward QA phantom 452. For example, in some embodiments, QA phantom 452 is a flat, rectangular phantom that is configured for measurements or tests in which an imaging panel (e.g., imaging panel 107 or EPID 105, shown in FIG. 1) is statically positioned on one side of QA phantom 452 and a kV or MV source (e.g., X-ray source 106 or LINAC 104, shown in FIG. 1) is statically positioned on an opposite side of QA phantom 452. Thus, in the embodiment illustrated in FIG. 7, no components of phantom holder 400 and no other QA phantoms are disposed in active area 752.

Figure 8:
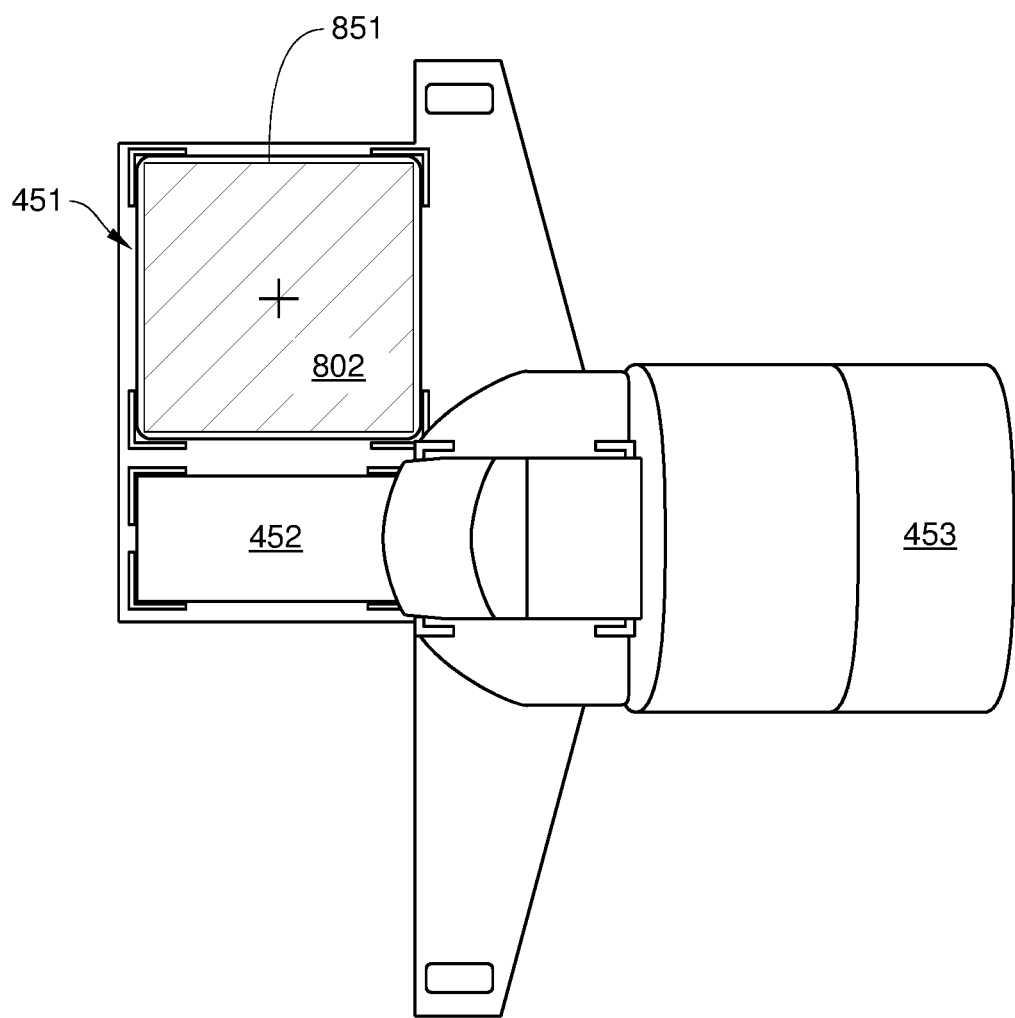
FIG. 8 is a plan view of a phantom holder and active areas associated with a quality assurance phantom, according to various embodiments.

FIG. 8 is a plan view of phantom holder 400 and active areas associated with QA phantom 451, according to various embodiments. As shown, QA phantom 451 has an associated active area 851 (cross-hatched) that extends away from a horizontal surface 802 of QA phantom 451. In the embodiment illustrated in FIG. 8, active area 851 indicates a region adjacent to QA phantom 451 through which, during certain measurements or tests, ionizing radiation is directed toward QA phantom 451. For example, in some embodiments, QA phantom 451 is a flat, rectangular phantom that is configured for measurements or tests in which an imaging panel (e.g., imaging panel 107 or EPID 105, shown in FIG. 1) is statically positioned on one side of QA phantom 451 and a kV or MV source (e.g., X-ray source 106 or LINAC 104, shown in FIG. 1) is statically positioned on an opposite side of QA phantom 451. In the embodiment illustrated in FIG. 8, QA phantom 451 is oriented so that no other QA phantoms are disposed in active area 851.

Figure 9:
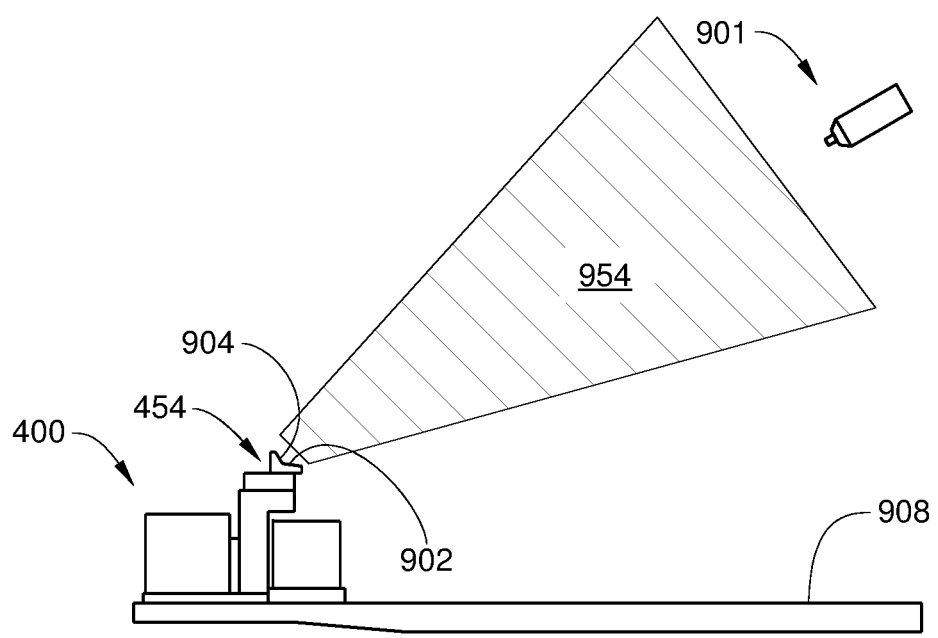
FIG. 9 is a side view of a phantom holder positioned on a treatment couch and active areas associated with a quality assurance phantom, according to various embodiments.

FIG. 9 is a side view of phantom holder 400 positioned on a treatment couch 908 and active areas associated with QA phantom 454, according to various embodiments. As shown, QA phantom 454 has an associated active area 954 (crosshatched) that extends away from a surface 904 of QA phantom 454. In the embodiment illustrated in FIG. 9, QA phantom 454 is configured to simulate patient motion caused by respiration. Consequently, active area 954 indicates a region adjacent to QA phantom 454 through which, during certain measurements or tests, one or more optical devices 901 of a radiation therapy system monitor QA phantom 454. For example, in some embodiments, QA phantom 454 includes a movable plate 902, and certain measurements or tests typically require an unobstructed line of sight between movable plate 902 and the one or more optical devices 901. As shown, phantom holder 400 is configured to position movable plate 902 and QA phantom 454 so that no other QA phantoms are disposed in active area 954. Optical sensors 901 can include one or more cameras, optical motion or proximity sensors, and/or the like. In some embodiments, one or more of optical sensors 901 are integrated into the radiation therapy system that includes treatment couch 908. Alternatively or additionally, in some embodiments, one or more of optical sensors 901 are included in a separate system from the radiation therapy system that includes treatment couch 908, such as a standalone system.

In the embodiment illustrated in FIG. 9, active area 954 is depicted as a triangular region. In embodiments in which treatment couch 908 can rotate, pitch, roll, and/or translate relative to an isocenter of a radiation therapy system (as shown in FIG. 3), active area 954 can include a three-dimensional region that corresponds to the rotation of the two-dimensional region shown in FIG. 9 about the isocenter of the radiation therapy system (e.g., isocenter 203 in FIG. 2). Thus, in such embodiments, active area 954 can include a three-dimensional region between the one or more optical devices 901 and various orientations or positions of movable plate 902. Alternatively or additionally, in embodiment in which a test routine that involves the positioning of QA phantom 454 in multiple locations, active area 954 can include multiple three-dimensional regions between the one or more optical devices 901 and the various orientations or positions of movable plate 902.

Returning to FIGS. 4, 5, and 6, the one or more positioning elements 410 of phantom holder 400 are configured to precisely position each of QA phantoms 450 in a different specific location and orientation relative to couch 408. In some embodiments, phantom holder 400 includes at least one positioning element 410 for each QA phantom 450 to be supported by phantom holder 400. For example, in the embodiment illustrated in FIGS. 5, 6, and 7, positioning elements 411-414 are configured to position QA phantom 451 in a first position, positioning elements 415-418 are configured to position QA phantom 452 in a second position, positioning elements 419-421 are configured to position QA phantom 453 in a third position, and positioning elements 422-425 are configured to position QA phantom 454 in a fourth position. In other embodiments, one or more of positioning elements 410 can position multiple QA phantoms 450.

In some embodiments, positioning elements 410 can be formed as a single component with base 401, for example via injection molding and/or a three-dimensional printing process. In other embodiments, positioning elements 410 can include separate components that are welded, glued, or otherwise affixed to base 401. Alternatively or additionally, in some embodiments, positioning features of one or more positioning elements 410 are machined to have higher positioning accuracy. For example, in some embodiments, one or more surfaces of positioning elements 410 are machined that are configured to contact a surface of a QA phantom 410 when the QA phantom is supported by phantom holder 400. In other embodiments, an injection-molding or three-dimensional printing process generates positioning elements 410 with surfaces that have sufficient positioning accuracy for positioning QA phantoms 410.

One or more coupling elements 431 and 432 of phantom holder 400 are each configured to mate with a respective indexing feature of a patient treatment couch of a radiation therapy system, such as patient treatment couch 408. Thus, in the embodiment illustrated in FIG. 5, coupling element 431 is configured to mate with an indexing feature 531 and coupling element 432 of patient treatment couch 408 is configured to mate with an indexing feature 532 of patient treatment couch 408. As a result, when coupling element 431 is in contact with indexing feature 531 and coupling element 432 is in contact with indexing feature 532, a position of base 401 (and therefore QA phantoms 450) relative to patient treatment couch 408 is fixed in a known location.

In the embodiment illustrated in FIGS. 4, 5, and 6, coupling elements 431 and 432 each include a projecting feature configured to mate with a complementary feature, such as a hole, dimple, depression, or slot. Thus, in such embodiments, indexing features 531 and 532 are each configured with such a complementary feature. In other embodiments, any other technically feasible configuration of coupling elements and indexing features can be employed so that coupling elements 431 and 432 fix a position of base 401 relative to patient treatment couch 408.

In the embodiment illustrated in FIGS. 4, 5, and 6, coupling element 431 is disposed on a first side 501 of base 401 and coupling element 432 is disposed on a second side 502 of base 401 that is an opposite side from the first side. Thus, in such embodiments, indexing feature 531 is disposed on one side of patient treatment couch 408 and indexing feature 532 is disposed on an opposite side of patient treatment couch 408. In other embodiments, phantom holder 400 includes more than two coupling elements or a single coupling element.

In some embodiments, coupling element 431 and coupling element 432 are removable components of phantom holder 400. In such embodiments, coupling elements 431 and 432 are configured to fix a position of base 401 relative to a particular patient treatment couch (such as patient treatment couch 408), while other coupling elements (not shown) are configured to fix a position of base 401 relative to a different patient treatment couch than patient treatment couch 408. Additionally or alternatively, in some embodiments, coupling element 431 and coupling element 432 are configured to be adapted to multiple different patient treatment couches 408. In such embodiments, coupling element 431 and coupling element 432 may not be removable components, and instead are adjustable components of phantom holder 400. Thus, in such embodiments, phantom holder 400 can be employed on multiple different patient treatment couches that each have different indexing features.

Automated Sequencing of Multiple QA Processes Using Phantom Holder

Because phantom holder 400 supports multiple QA phantoms 450 in known, pre-defined locations and orientations, embodiments of phantom holder 400 enable an automated sequence of multiple QA processes to be performed on multiple QA phantoms. As a result, a sequence of multiple QA processes can be performed on a radiation therapy system without the clinician returning to the treatment room for each QA phantom that is employed in the sequence of multiple QA processes. One such embodiment is described below in conjunction with FIG. 10.

Figure 10:
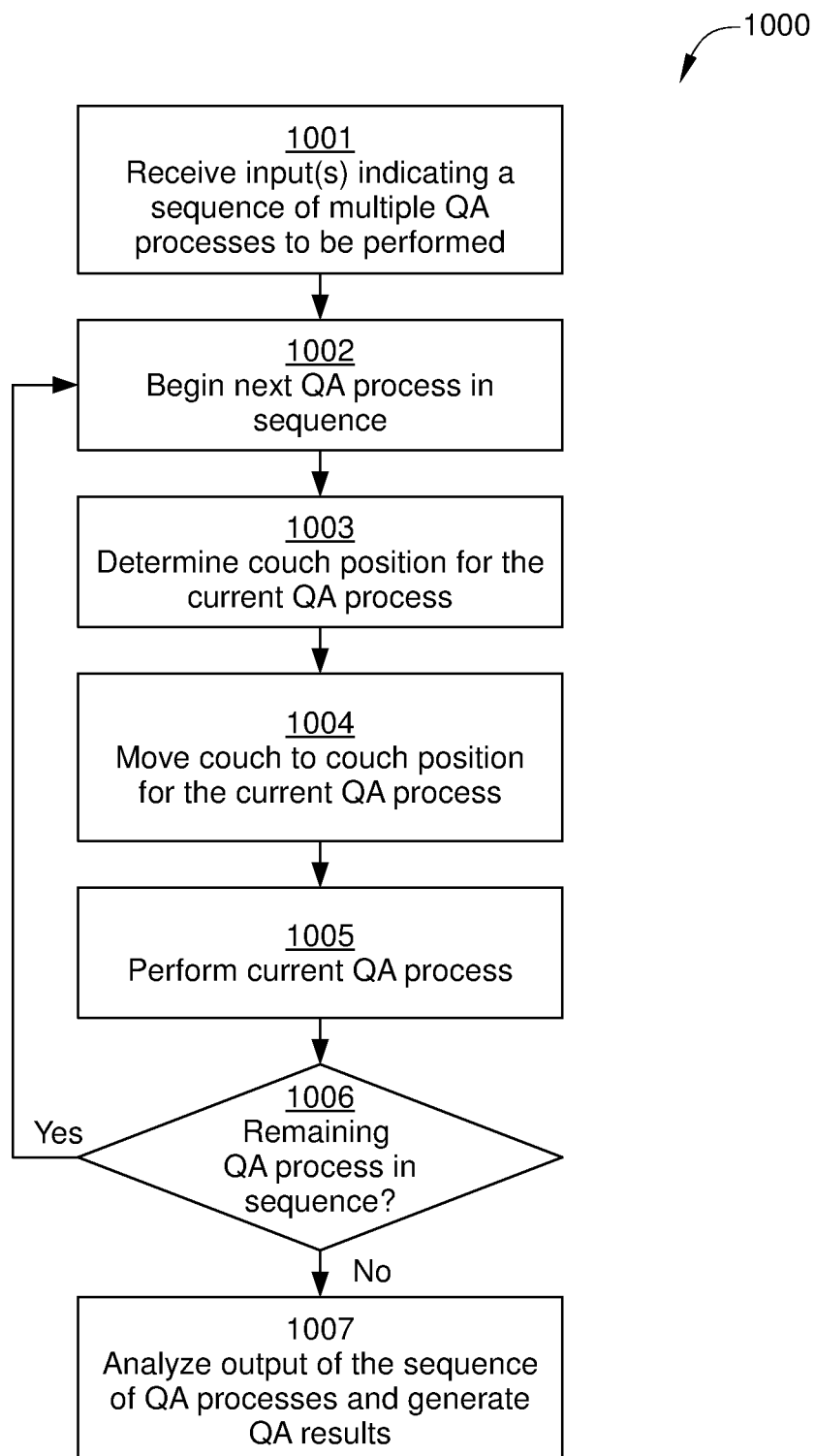
FIG. 10 sets forth a flowchart of a computer-implemented method 1000 for a radiation therapy system configured with a phantom holder, according to one or more embodiments.

FIG. 10 sets forth a flowchart of a computer-implemented method 1000 for a radiation therapy system configured with phantom holder 400, according to one or more embodiments. Computer-implemented method 1000 may include one or more operations, functions, or actions, as illustrated by one or more of blocks 1001-1007. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although computer-implemented method 1000 is described in conjunction with RT system 100 of FIGS. 1-3 and phantom holder 400 of FIGS. 4-6, persons skilled in the art will understand that any suitably configured X-ray imaging system is within the scope of the present embodiments.

The control algorithms for the blocks of computer-implemented method 1000 may be performed by any suitable computing device or devices. For example, in some embodiments, some or all of the control algorithms for the blocks of computer-implemented method 1000 reside in image acquisition and treatment control computer 109, remote control console 111, a combination of both, or any other computing device communicatively coupled to RT system 100. The control algorithms can be implemented in whole or in part as software- or firmware-implemented logic, and/or as hardware-implemented logic circuits.

Prior to computer-implemented method 1000, a clinician or other user positions phantom holder 400 on couch 108 while couch phantom holder 400 supports multiple QA phantoms 450. Because coupling elements 431 and 432 fix a position of phantom holder 400 relative to couch 108, RT system 100 can locate a specific QA phantom 450 at a particular test location as part of an automated QA process via automated motion of couch 108. RT system 100 can then locate a different QA phantom 450 at a different test location as part of the same automated QA process via automated motion of couch 108.

In step 1001, RT system 100 receives one or more user inputs indicating a sequence of multiple QA processes to be performed, such as a specific QA testing protocol. Alternatively, the user inputs can generate a new QA testing protocol that includes multiple QA processes. Examples of such QA processes include a measurement or test that employs a static position of an imaging system, a measurement or test that employs a dynamic use of an imaging system via rotation of C-arm gantry 110 about a QA phantom 450, a measurement or test that employs optical sensors of radiation therapy system, such as optical devices 901, a measurement or test that employs directing ionizing radiation at a QA phantom 450, a measurement or test that employs EPID 105 (such as determining the mechanical operation and accuracy of EPID 105), and/or the like.

In step 1002, RT system 100 begins the next QA process in the sequence of multiple QA processes to be performed. In step 1003, RT system 100 determines a couch position for the current QA process. In some embodiments, the couch position for a particular QA process is based on a user input received in step 1001. In other embodiments, the couch position for a particular QA process is included in the specific protocol that corresponds to the sequence of multiple QA processes being performed.

In step 1004, RT system 100 moves couch 108 to the couch position for the current QA process that is determined in step 1003. By moving couch 108 to the couch position for the current QA process, phantom holder 400 is positioned so that a QA phantom 450 that is associated with the current QA process is disposed at a test location associated with the current QA process. For example, in some instances, the test location is a position relative to RT system 100 that provides an unobstructed line of sight between movable plate 902 and one or more optical devices 901. In some instances, the test location is a position relative to RT system 100 that enables a CBCT measurement to be performed that involves rotation of C-arm gantry 110 about the QA phantom 450 associated with the current QA process. In some instances, the test location is a position relative to RT system 100 that enables a static positioning of an imaging system of RT system 100 proximate the QA phantom 450 associated with the current QA process. In step 1005, RT system 100 performs the current QA process using the QA phantom 450 associated with the current QA process.

In step 1006, RT system 100 determines whether there are any remaining QA processes in the sequence of multiple QA processes to be performed. If yes, computer-implemented method 1000 returns to step 1002; if no, computer-implemented method 1000 proceeds to step 1007. In step 1007, RT system 100 and/or an associated computing device analyzes output of the sequence of QA processes and generates QA results for each QA process. Alternatively, in some embodiments, RT system 100 and/or an associated computing device performs the analysis and generation of QA results for each individual QA process after step 1005 of computer-implemented method 1000.

Implementation of computer-implemented process 1000 enables multiple QA processes to be performed in a single automated sequence. Thus, embodiments described herein obviate the need for a clinician or other user to repeatedly reenter a treatment room to position a particular QA phantom for each QA process to be performed on RT system 100. Instead, multiple QA processes are performed in a single automated sequence.

Exemplary Computing Device

Figure 11:
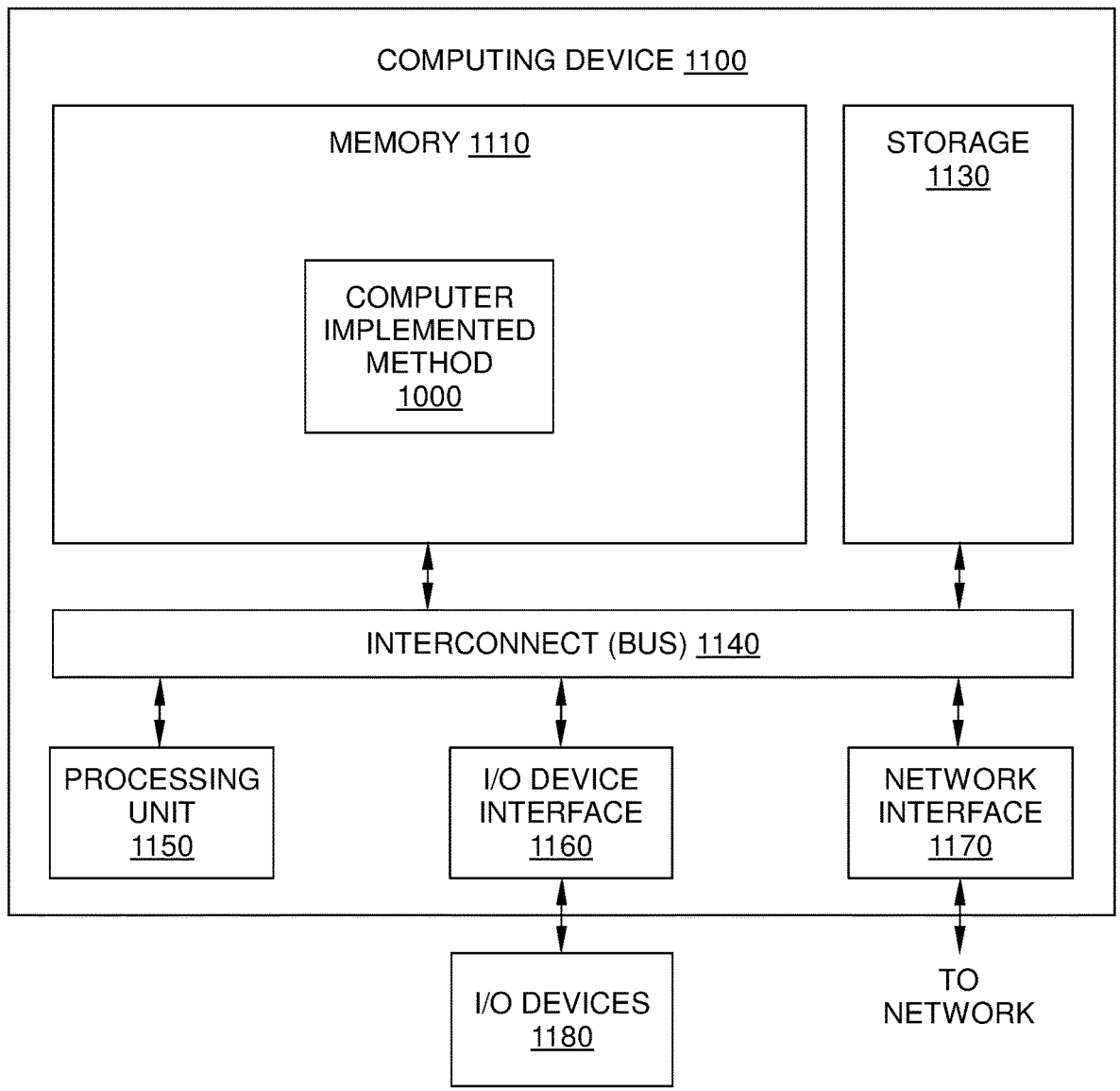
FIG. 11 is an illustration of computing device configured to perform various embodiments.

FIG. 11 is an illustration of a computing device 1100 configured to perform various embodiments. Computing device 1100 may be a desktop computer, a laptop computer, a smart phone, or any other type of computing device suitable for practicing one or more embodiments of the present disclosure, including image acquisition and treatment control computer 109 and/or remote control console 111. In operation, computing device 1100 is configured to execute instructions associated with computer-implemented method 1000 as described herein. It is noted that the computing device described herein is illustrative and that any other technically feasible configurations fall within the scope of the present disclosure.

As shown, computing device 1100 includes, without limitation, an interconnect (bus) 1140 that connects a processing unit 1150, an input/output (I/O) device interface 1160 coupled to input/output (I/O) devices 1180, memory 1110, a storage 1130, and a network interface 1170. Processing unit 1150 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 1150 may be any technically feasible hardware unit capable of processing data and/or executing software applications, including computer-implemented method 1000.

I/O devices 1180 may include devices capable of providing input, such as a keyboard, a mouse, a touch-sensitive screen, and so forth, as well as devices capable of providing output, such as a display device and the like. Additionally, I/O devices 1180 may include devices capable of both receiving input and providing output, such as a touchscreen, a universal serial bus (USB) port, and so forth. I/O devices 1180 may be configured to receive various types of input from an end-user of computing device 1100, and to also provide various types of output to the end-user of computing device 1100, such as displayed digital images or digital videos. In some embodiments, one or more of I/O devices 1180 are configured to couple computing device 1100 to a network.

Memory 1110 may include a random access memory (RAM) module, a flash memory unit, or any other type of memory unit or combination thereof. Processing unit 1150, I/O device interface 1160, and network interface 1170 are configured to read data from and write data to memory 1110. Memory 1110 includes various software programs that can be executed by processor 1150 and application data associated with said software programs, including computer-implemented method 1000.

Exemplary Computer Program Product

Figure 12:
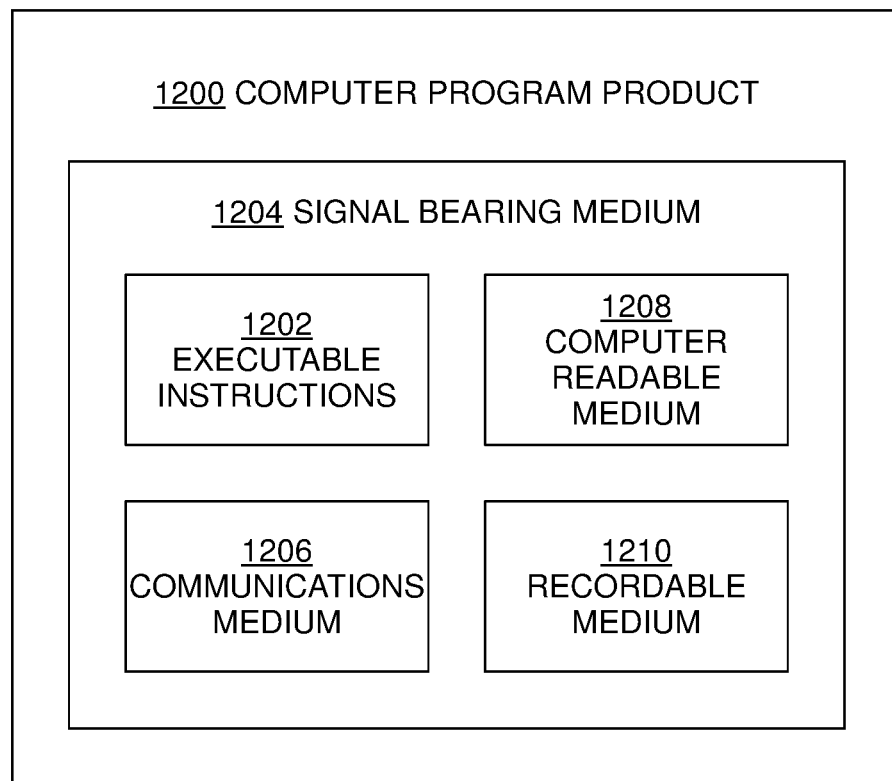
FIG. 12 is a block diagram of an illustrative embodiment of a computer program product for implementing a method for segmenting an image, according to one or more embodiments.

FIG. 12 is a block diagram of an illustrative embodiment of a computer program product 1200 for implementing a method for segmenting an image, according to one or more embodiments. Computer program product 1200 may include a signal bearing medium 1204. Signal bearing medium 1204 may include one or more sets of executable instructions 1202 that, when executed by, for example, a processor of a computing device, may provide at least the functionality described above with respect to FIGS. 1-10.

In some implementations, signal bearing medium 1204 may encompass a non-transitory computer readable medium 1208, such as, but not limited to, a hard disk drive, a Compact Disc (CD), a Digital Video Disk (DVD), a digital tape, memory, etc. In some implementations, signal bearing medium 1204 may encompass a recordable medium 1210, such as, but not limited to, memory, read/write (R/W) CDs, R/W DVDs, etc. In some implementations, signal bearing medium 1204 may encompass a communications medium 1206, such as, but not limited to, a digital and/or an analog communication medium (e.g., a fiber optic cable, a waveguide, a wired communications link, a wireless communication link, etc.). Computer program product 1200 may be recorded on non-transitory computer readable medium 1208 or another similar recordable medium 1210.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, a solid-state drive, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. An apparatus in a radiation therapy system, the apparatus comprising:
a base configured to support a first quality assurance phantom at a first position and a second quality assurance phantom at a second position;
a first coupling element that comprises a first removable component that mates with a first indexing feature on a first side of a first patient treatment couch and a third removable component that mates with a third indexing feature on a first side of a second patient treatment couch; and
a second coupling element that comprises a second removable component that mates with a second indexing feature on a second side of the first patient treatment couch and a fourth removable component that mates with a fourth indexing feature on a second side of the second patient treatment couch,
wherein the first coupling element is disposed on a first side of the base, the second coupling element is disposed on a second side of the base, and the first side of the base is an opposite side to the second side of the base, wherein the first removable component and the second removable component fix a position of the base relative to the first patient treatment couch, wherein the third removable component and the fourth removable component fix a position of the base relative to the second patient treatment couch, and wherein the first removable component does not mate with the third indexing feature on the first side of the second patient treatment couch.

2. The apparatus of claim 1, wherein the first position is disposed outside a second active area of the second quality assurance phantom and the second position is disposed outside a first active area of the first quality assurance phantom.

3. The apparatus of claim 2, wherein the first active area includes a line of sight between the first quality assurance phantom and at least one optical sensor associated with the radiation therapy system.

4. The apparatus of claim 2, wherein first quality assurance phantom comprises a cone-beam computed tomography phantom and the first active area includes one of a cylindrical region or a partial cylindrical region that is proximate the first quality assurance phantom.

5. The apparatus of claim 2, wherein the first active area includes a region through which ionizing radiation is directed toward the first quality assurance phantom during a quality assurance process associated with the radiation therapy system.

6. The apparatus of claim 2, wherein the base is disposed outside the first active area and the second active area.

7. The apparatus of claim 1, wherein the base comprises a radiologically transparent material.

8. The apparatus of claim 1, wherein the second patient treatment couch is associated with the radiation therapy system.

9. The apparatus of claim 1, wherein the second patient treatment couch is associated with a different radiation system than the radiation therapy system.

10. The apparatus of claim 1, wherein the base includes at least one positioning element for positioning the first quality assurance phantom at the first position and at least one positioning element for positioning the second quality assurance phantom at the second position.

11. The apparatus of claim 10, wherein the at least one positioning element for positioning the first quality assurance phantom at the first position comprises a radiologically transparent material.

12. The apparatus of claim 10, wherein the at least one positioning element for positioning the first quality assurance phantom at the first position is disposed outside a first active area of the first quality assurance phantom and a second active area of the second quality assurance phantom.

13. An apparatus in a radiation therapy system, the apparatus comprising:

a base configured to support a first quality assurance phantom at a first position and a second quality assurance phantom at a second position; and at least one coupling element that is configured to:
 mate with at least one indexing feature of a first patient treatment couch of the radiation therapy system; and
 fix a position of the base relative to the first patient treatment couch, wherein the at least one coupling element comprises a first removable component that mates with the at least one indexing feature of the first patient treatment couch and a second removable component that mates with at least one indexing feature of a second patient treatment couch, and wherein the first removable component does not mate with the at least one indexing feature of the second patient treatment couch.

14. The apparatus of claim 13, wherein the first position is disposed outside a second active area of the second quality assurance phantom and the second position is disposed outside a first active area of the first quality assurance phantom.

15. The apparatus of claim 14, wherein the first active area includes a line of sight between the first quality assurance phantom and at least one optical sensor associated with the radiation therapy system.

16. The apparatus of claim 13, wherein the base comprises a radiologically transparent material.

17. The apparatus of claim 13, wherein the second patient treatment couch is associated with the radiation therapy system.

18. The apparatus of claim 13, wherein the second removable component does not mate with the at least one indexing feature of the first patient treatment couch.

19. An apparatus in a radiation therapy system, the apparatus comprising:

a base configured to support a first quality assurance phantom at a first position and a second quality assurance phantom at a second position; and at least one coupling element that is configured to:
 mate with at least one indexing feature of a first patient treatment couch of the radiation therapy system; and
 fix a position of the base relative to the first patient treatment couch, wherein the at least one coupling element comprises a first removable component that mates with the at least one indexing feature of the first patient treatment couch and a second removable component that mates with at least one indexing feature of a second patient treatment couch, and wherein the first removable component does not mate with the at least one indexing feature of the second patient treatment couch and the second removable component does not mate with the at least one indexing feature of the first patient treatment couch.

\* \* \* \* \*